United States Patent [19]

Mikhail

[11] 4,380,464

[45] Apr. 19, 1983

[54] N,N-DIACYLAMINOPERFLUOROALK-ANESULFONANILIDES AND DERIVATIVES THEREOF

[75] Inventor: Ezzat A. Mikhail, New Brighton, Minn.

[73] Assignee: Minnesota Mining and Manufacturing Company, St. Paul, Minn.

[21] Appl. No.: 345,738

[22] Filed: Feb. 4, 1982

Related U.S. Application Data

[63] Continuation-in-part of Ser. No. 188,535, Sep. 18, 1980, abandoned.

[51] Int. Cl.³ .................. C07C 143/83; C07C 143/75; A01N 41/06
[52] U.S. Cl. ............................................ 71/88; 71/90; 71/94; 71/100; 71/103; 260/455 A; 546/314; 546/315; 549/72; 549/487; 560/13; 564/97; 71/95
[58] Field of Search ......................... 260/455 A, 347.2; 546/314, 315; 549/72, 487; 560/13; 564/97; 71/88, 90, 94, 95, 100, 103

[56] References Cited

U.S. PATENT DOCUMENTS

| | | | |
|---|---|---|---|
| 3,639,474 | 2/1972 | Kenneth | 260/556 F |
| 3,725,451 | 4/1973 | Trancik | 560/13 |
| 3,799,968 | 3/1974 | Harrington | 564/97 |
| 3,894,078 | 7/1975 | Fridinger | 260/501.19 |
| 3,895,062 | 7/1975 | Harrington | 564/97 |
| 4,005,141 | 1/1977 | Moore | 560/13 |

*Primary Examiner*—Michael L. Shippen
*Attorney, Agent, or Firm*—Cruzan Alexander; Donald M. Sell; Lorraine R. Sherman

[57] ABSTRACT

Disclosure is made of certain optionally substituted N,N-diacylaminoperfluoroalkanesulfonanilides and agriculturally acceptable salts thereof which are useful as herbicides and plant growth regulators.

23 Claims, No Drawings

N,N-DIACYLAMINOPERFLUOROALKANESULFONANILIDES AND DERIVATIVES THEREOF

This application is a continuation-in-part of copending application Ser. No. 188,535, filed Sept. 18, 1980, now abandoned.

TECHNICAL FIELD

This invention relates to certain optionally substituted N,N-diacylaminoperfluoroalkanesulfonanilides and agriculturally acceptable salts thereof which are useful as herbicides and plant growth regulators.

BACKGROUND ART

Various N-substituted perfluoroalkanesulfonamides are described in U.S. Pat. No. 3,639,474 as active herbicides and plant growth modifiers. 5-acetamido-2-methyltrifluoromethanesulfonanilide and 5-acetamido-2-chlorotrifluoromethanesulfonanilide are particularly disclosed therein to have plant growth modifying activity, including the ability to retard the growth of grass without significant distortion of the normal foliar shape. (This plant growth modifying activity is of interest because it reduces the number of times grass must be mowed.) U.S. Pat. No. 3,894,078 teaches the compound 5-acetamido-2,4-dimethyl-trifluoromethanesulfonanilide and its use a plant growth regulator. However, no N,N-diacylaminoperfluoroalkanesulfonanilide has been reported.

DISCLOSURE OF INVENTION

The present invention relates to compounds of the formula:

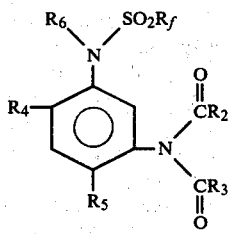

wherein
$R_f$ is lower perfluoroalkyl;
$R_2$ and $R_3$ each independently is
(1) a hydrocarbon group selected from alkyl, alkenyl, cycloalkyl, phenyl, and substituted phenyl,
(2) haloalkyl,
(3) alkoxy, and
(4) a heterocyclic group which can contain only carbon, hydrogen, oxygen, nitrogen, and sulfur, but which must contain at least one ring atom selected from oxygen, nitrogen, and sulfur;
$R_4$ and $R_5$ each independently is hydrogen, alkyl, or halo; and
$R_6$ is hydrogen, alkoxycarbonyl, (alkylthio)carbonyl, (haloalkylthio)carbonyl, haloalkoxycarbonyl, or phenoxycarbonyl;
and agriculturally acceptable salts of the acid form compounds (those compounds of the invention in which $R_6$ is hydrogen); provided that
$R_f$ contains not more than four carbon atoms,
$R_2$ and $R_3$ individually contain not more than nine carbon atoms,
$R_4$ and $R_5$ individually contain not more than four carbon atoms, and
$R_6$ contains not more than twelve carbon atoms.

The term "lower" herein means that the indicated group contains not more than four carbon atoms.

The term "substituted phenyl" herein means a phenyl group substituted by up to three groups selected from alkyl, alkoxy, alkylthio, mono- or dialkylamino, and halo, wherein each alkyl moiety has 1 to 4 carbon atoms.

Preferably, the compounds of formula I are those in which:
$R_f$ is trifluoromethyl;
$R_2$ and $R_3$ independently are alkyl, haloalkyl, cycloalkyl and alkoxy;
$R_4$ and $R_5$ independently are alkyl and halo; and
$R_6$ is hydrogen or alkoxycarbonyl;
provided that
$R_2$, $R_3$, $R_4$, $R_5$ and $R_6$ contain not more than four carbon atoms each, for a sum total of not more than twelve carbon atoms for these groups.

Particularly preferred (due to their relatively high preemergence herbicidal activity and their plant growth modifying or regulating activity) are the compounds of formula I in which:
$R_f$ is $CF_3$;
$R_2$ is $CH_3$, $C_2H_5$, or $n-C_4H_9$;
$R_3$ is $CH_3$, $OCH_2CH_3$, $CF_3$, $ClCH_2$, $Cl_2CH$, $n-C_4H_9$, or cyclopropyl;
$R_4$ and $R_5$ independently are Cl or $CH_3$; and
$R_6$ is H or

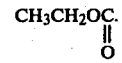

The acid form compounds of formula I, above, wherein $R_6$ is H, can form salts by replacement thereof by an agriculturally acceptable cation.

The invention also relates to methods for preparing the compounds, to methods for their use as herbicides, as plant growth regulators, and in herbicidal and plant growth regulating compositions which comprise the compounds dispersed in agriculturally acceptable extending media.

DETAILED DESCRIPTION

The compounds of the invention (*) can be prepared according to the reaction sequences outlined below, although, as will be seen, some variation is possible in the order of steps (1) through (4) followed in preparing the compounds of the invention.

FLOW CHART

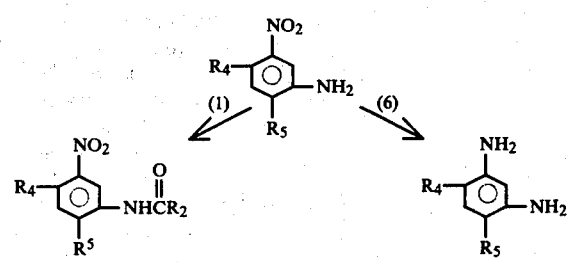

-continued
FLOW CHART

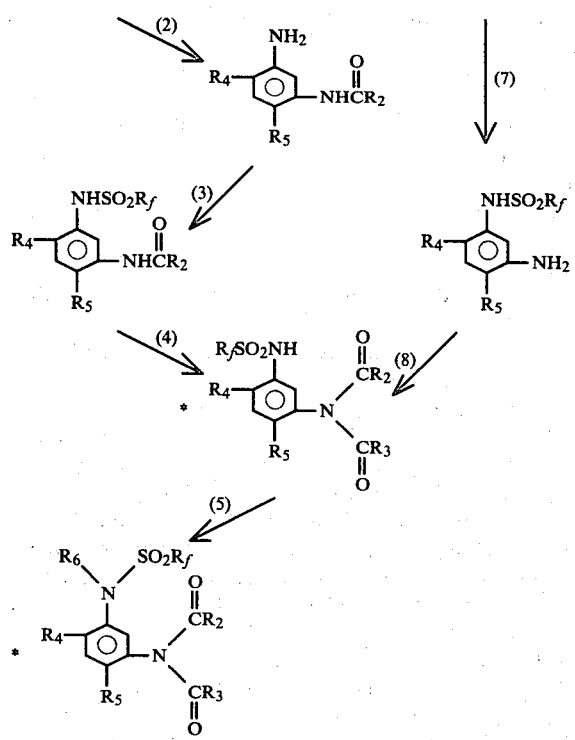

The starting materials for the process of the invention are nitroaniline and substituted nitroanilines. These compounds are themselves known to the art or may be prepared from known compounds by methods which are well known to the art, for example, by the nitration of a suitably substituted aniline derivative or selective reduction of the desired dinitroaniline derivative.

Step (1) of the flow chart is carried out by reacting the desired nitroaniline derivative with a slight excess of a compound of the formula $$R_2CQ,$$
$$\parallel$$
$$O$$

wherein Q is halogen, preferably chlorine, or an anhydride residue. The reaction may be carried out in suitable non-reactive solvents such as amides of organic acids (e.g., N,N-dimethylformamide), ethers (e.g., tetrahydrofuran), chlorinated hydrocarbons (e.g., ethylenedichloride) and the like. It can also be carried out in the absence of solvent. The reaction temperature may be from about 0° C. to 100° C., depending upon the rate of reaction desired. The reaction proceeds readily at room temperature (about 25° C.). The product is isolated by conventional methods.

Step (2) is a reduction of the nitro group of the intermediate acylaminonitro derivative. Chemical or catalytic methods well known to the art are successful. Raney nickel is a suitable catalyst for the reduction and the product is isolated by conventional methods.

The reaction of step (3) of the flow chart is carried out utilizing a solution of the appropriate primary arylamine and a suitable acid acceptor (such as triethylamine, N,N-dimethylaniline, pyridine and the like) in an inert organic solvent. However, an acid acceptor is not always necessary, and an excess of the primary arylamine may also serve as acid acceptor. Among the suitable solvents are 1,2-dimethoxyethane, benzene, chloroform, dichloromethane, dimethylacetamide, dimethylformamide and the like. Alternatively, an excess of the primary arylamine or the acid acceptor may serve as a solvent, or the reaction may be carried out in the absence of solvent. Generally, a slight excess of an equimolar quantity of the appropriate perfluoroalkane sulfonic anhydride or halide is added to the solution. The addition is advantageously carried out at −15° C. to 50° C., and for some reactants higher or lower temperature may be preferable. In cases where the amine is of lower reactivity, it is advantageous to allow the reaction mixture to remain at reflux temperature for a few hours following addition.

The reaction of step (3) may also be carried out in a high pressure reactor. This technique is particularly preferred when perfluoroalkanesulfonyl fluorides are used as reactants. These reactions are usually carried out at temperature ranges of 0° to 150° C., but these temperature ranges may be raised or lowered, depending upon the reactants used. Such reactions are most frequently carried out without solvent, or with dimethylformamide or excess triethylamine as solvent, but other advantageous variations are possible.

After completion of the reaction, the product is isolated by conventional methods. For example, the reaction mixture can be extracted with excess aqueous sodium hydroxide. The aqueous extract is then washed with organic solvents and treated with charcoal to remove impurities. Subsequent acidification of the aqueous extract with mineral acid then affords the product as an oil or solid which is distilled, sublimed, chromatographed or recrystallized as required to give the pure product. When water-soluble solvents are used, the reaction mixture can be poured directly into aqueous mineral acids. The product is then isolated by conventional extraction techniques and purified as above.

Step (4) is carried out by reacting the product of step (3) in the flow chart with a slight excess of the desired acyl derivative as in step (1).

Step (5) is carried out by reacting the product of step (4) of the flow chart with the corresponding alkyl chloroformate derivative in a suitable solvent, such as glyme, at its reflux temperature in the presence of the appropriate amount of base. The base is preferably an inorganic acid acceptor (e.g., $Na_2CO_3$ or a weak organic base such as N,N-dimethylcyclohexylamine) and the product is isolated by conventional methods.

In the alternative route shown on the flow chart, the reduction and sulfonation steps (6) and (7) are carried out under the conditions described previously for steps (2) and (3). If $R_2$ and $R_3$ are the same, the diacylation step (8) is carried out as described above for the precursor of step (1). If $R_2$ and $R_3$ are different, step (8) is ordinarily carried out as two separate reactions, e.g., analogously to steps (1) and (4).

The salts of the invention are generally metal, ammonium, and organic amine salts and can be prepared by treating the acid-form compound with an appropriate base under mild conditions. Among the metal salts of the invention are alkali metal (e.g., lithium, sodium, and potassium), alkaline earth metal (e.g., barium, calcium, and magnesium) and heavy metal (e.g., zinc and iron) salts as well as other metal salts such as aluminum. Appropriate bases for use in preparing the metal salts include metal oxides, hydroxides, carbonates, bicarbonates, and alkoxides. Some salts are also prepared by a cation exchange reaction (by reacting a salt of the invention with an organic or inorganic salt in a cation exchange reaction). The organic amine salts include the salts of aliphatic (e.g., alkyl), aromatic and heterocyclic amines, as well as those having a mixture of these types of structures. The amines useful in preparing the salts of the invention can be primary, secondary, or tertiary and preferably contain not more than 20 carbon atoms. Such amines include, for example, morpholine, N,N-dimethyl cyclohexylamine, glucosamine, amines derived from fatty acids, etc. The amine and ammonium salts can be prepared by reacting the acid form with the appropriate organic base or ammonium hydroxide. Any of the salts of the types set out above are agriculturally acceptable, the one chosen depending upon the particular use and upon the economics of the situation. Of particular utility are the alkali metal, alkaline earth, ammonium and amine salts.

The salts of the invention are frequently formed by reacting the precursors in aqueous solution. This solution can be evaporated to obtain the salt of the compound, usually as a dry powder. In some cases, it may be more convenient to use a non-aqueous solvent such as alcohols, acetone, etc. The resulting solution is then treated to remove the solvent, for example, by evaporation under reduced pressure.

It will be appreciated that the scope of this invention encompasses starting materials of a wide range of physical and chemical properties, and the synthetic methods discussed herein are described in general and preferred language. However, a great variation in the use of these synthetic techniques is possible, and this invention is broadly inclusive of such variations.

The herbicidal activity of the compounds of the invention has been determined using screening tests against greenhouse plantings. Both pre- and post-emergence examples of weeds which were used for these tests.

Grasses:
   Giant Foxtail (*Setaria faberii*)
   Barnyard grass (*Echinochloa crusgalli*)
   Crabgrass (*Digitaria ischaemum*)
   Quackgrass (*Agopyron repens*)
   Yellow Nutsedge (*Cyperus esculentus*)
Broadleaves:
   Pigweed (*Amaranthus retroflexus*)
   Purslane (*Portulaca oleracea*)
   Wild Mustard (*Brassica kaber*)
   Wild Morning Glory (*Convolvulus arvensis*)

The test chemicals were dissolved in a small amount of acetone or other suitable solvent and then diluted with water to give a concentration of 2000 ppm. From this concentration aliquots were diluted to give a final concentration of 500 ppm. Eighty ml. of this solution were added to a 6-inch pot containing the weed seeds to give a concentration equivalent to 20 lb/acre. Use of 20 ml. of said solution gave a concentration equal to 5 lb/acre. All subsequent waterings were made from the bottom. Two pots were used per treatment. Data were taken 2 to 3 weeks after treatment and recorded as percent pre-emergence kill for each species compared to the untreated controls.

To assess post-emergence activity, the same weed mixtures were allowed to grow from two to three weeks until the grasses were approximately 1 to 3 inches and the broadleaves 1 to 1½ inches tall. They were sprayed for approximately 10 seconds or until good wetting of the leaf surfaces occurred with a 2000 ppm solution as described above.

The compounds of this invention are broadly active as herbicides. In addition, the compounds of this invention show various types of plant growth modifying activity. Plant growth modification as defined herein consists of all deviations from natural development, for example, defoliation, stimulation, stunting, retardation, desiccation, tillering, dwarfing, regulation, and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants.

For application to plants, the compounds can be finely divided and suspended in any of the usual aqueous media. In addition, spreading agents, wetting agents, sticking agents or other adjuvants can be added as desired. Dry powders, as such, or diluted with inert materials such as diatomaceous earth, can likewise be used as dusts for this purpose. The preparations are coated on the plants or the ground is covered when pre-emergence control is desired. Application is made with the usual sprayers, dust guns and the like. Application rates are at 0.5 to 20 lbs/acre in general, but may be increased or reduced according to individual circumstances of use.

The compounds of the invention may be used alone or in certain instances it may be advantageous to combine them with other known herbicides to broaden or maximize the weed spectrum controlled by herbicidal compositions of this invention or to better control a weed not well controlled by specific compounds of the invention. Furthermore, herbicidal compositions containing compounds of the invention may contain, in addition, nematicides, fungicides, insecticides, fertilizers, trace metals, soil conditioners, other plant growth regulators, and the like. Such combinations are clearly envisioned in this invention.

The following examples are given for the purpose of further illustrating the present invention but are not intended, in any way, to be limiting the scope thereof. All parts are given by weight unless otherwise specifically noted. The individual infrared spectra coincide with the assigned structures.

EXAMPLE 1

Preparation of 2,4-dimethyl-5-nitroacetanilide, using step (1).

To a solution of 2,4-dimethyl-5-nitroaniline (16.6 g., 100 mmoles) in methylene chloride (25 ml.), acetic anhydride (14.3 g., 120 mmoles) was added dropwise at 10° to 15° C. The reaction mixture was allowed to come to room temperature and was stirred for 15 minute, whereupon a precipitate started to form. The reaction mixture was heated to reflux for 60 minutes, and was then cooled to 5° to 10° C. The product was collected by filtration, and was washed with hexane. This gave 2,4-dimethyl-5-nitroacetanilide, m.p. 160°–164° C.

| Elementary analysis: | |
|---|---|
| FOUND | CALCULATED |
| C  58.1; | C  57.7; |
| H  5.9; | H  5.8; |

-continued

| Elementary analysis: | |
|---|---|
| FOUND | CALCULATED |
| N 13.6. | N 13.4. |

EXAMPLE 2

Preparation of 5-amino-2,4-dimethylacetanilide, step (2).

2,4-Dimethyl-5-nitroacetanilide (20.8 g., 100 mmole) in ethanol (400 ml.) was reduced over Raney nickel at about 45 psi of hydrogen gas. After the hydrogen uptake was complete, the mixture was deactivated with elementary sulfur, filtered, and the filtrate was evaporated under reduced pressure to give the product as a solid, m.p. 163°-164° C.

| Elementary analysis: | | |
|---|---|---|
| FOUND | | CALCULATED |
| C 67.3; | C | 67.4; |
| H 8.0; | H | 7.9; |
| N 15.5. | N | 15.7. |

EXAMPLE 3

Preparation of 5-acetamido-2,4-dimethyltrifluoromethanesulfonanilide, using step (3).

Trimethylamine (174 g., 2.95 mole), trifluoromethanesulfonyl fluoride (129 g., 0.826 mole), ethyl acetate (175 ml.) and 5-amino-2,4-dimethylacetanilide (105 g., 0.59 mole) were heated for about 1 day in a pressure vessel. The reaction mixture was then dissolved in about 1 liter of ten percent sodium hydroxide solution. The resulting solution was steam distilled until no basic distillate was obtained. The residual solution was cooled with an ice bath, then filtered to remove insoluble impurities. The filtrate was extracted twice with 500 ml. portions of dichloromethane. The aqueous phase was filtered, then the filtrate was cooled with an ice bath and acidified with cold dilute hydrochloric acid to provide a light yellow solid. The product was washed with water and dried to provide 155 g. (85%) of 5-acetamido-2,4-dimethyltrifluoro-methanesulfonanilide, m.p. 170°-176° C. Further purification was effected by recrystallization from acetonitrile to provide the product with m.p. 181°-184° C.

| Elementary analysis: | | |
|---|---|---|
| FOUND | | CALCULATED |
| C 42.4; | C | 42.6; |
| H 4.2; | H | 4.2; |
| N 8.9. | N | 9.0. |

An alternative work-up of the reaction mixture from the pressure reactor was to pour it into dilute hydrochloric acid. The product was filtered or extracted with organic solvents.

EXAMPLE 4

Preparation of 5-(N,N-diacetyl)amino-2,4-dimethyltrifluoromethanesulfonanilide, step (4).

5-Acetamido-2,4-dimethyltrifluoromethanesulfonanilide (3.1 g., 10 mmole) in 1,2-dichloroethane (40 ml.) was stirred while adding acetic anhydride (1.2 g., 12 mmole). The reaction mixture was heated to its reflux temperature for 18 hours, filtered hot and the filtrate cooled. The resulting precipitate was collected by filtration, to give a white solid, m.p. 172°-173° C.

| Elementary analysis: | |
|---|---|
| FOUND | CALCULATED |
| C 44.1; | C 44.3; |
| H 4.3; | H 4.3; |
| N 7.9; | N 8.0. |

The following compounds were prepared utilizing the steps of examples (1-4), but substituting appropriate precursors:

2,4-Dimethyl-5-[N-(2'-furoyl)-N-acetyl]aminotrifluoromethanesulfonanilide, m.p. 160°-163° C.

5-(N-acetyl-N-trifluoroacetyl)amino-2,4-dimethyltrifluoromethanesulfonanilide, m.p. 145°-147° C.

5-(N-acetyl-N-dichloroacetyl)amino-2,4-dimethyltrifluoromethanesulfonanilide, m.p. 127°-129° C.

5-(N-acetyl-N-chloroacetyl)amino-2,4-dimethyltrifluoromethanesulfonanilide, m.p. 147°-150° C.

5-(N-acetyl-N-valeryl)amino-2,4-dimethyltrifluoromethanesulfonanilide, m.p. 120°-125° C.

5-(N-chloroacetyl-N-trifluoroacetyl)amino-2,4-dimethyltrifluoromethanesulfonanilide, m.p. 173°-175° C.

5-(N-acetyl-N-cyclopropanecarbonyl)amino-2,4-dimethyltrifluoromethanesulfonanilide, m.p. 172°-174° C.

Similarly, the following compounds can be prepared, by utilizing appropriate precursors:

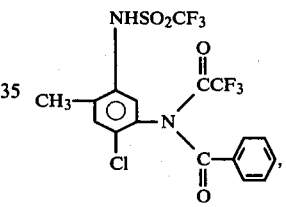

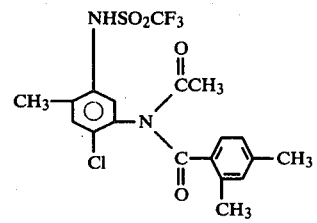

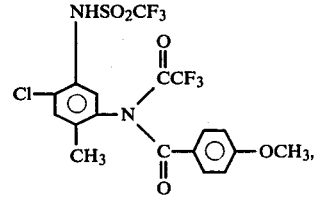

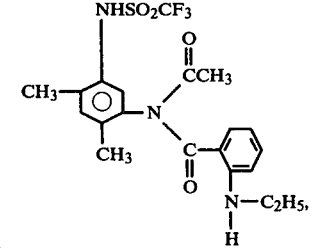

-continued

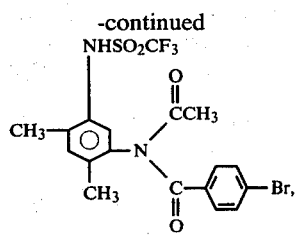

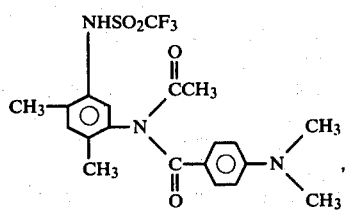

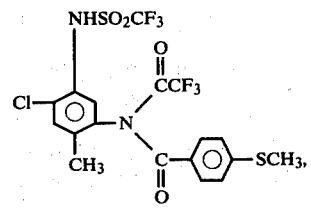

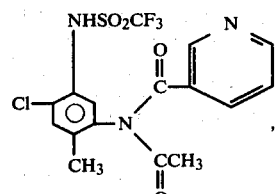

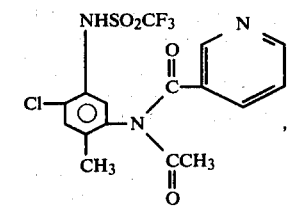

EXAMPLE 5

Preparation of 5-(N-acetyl-N-ethoxycarbonyl)amino-2,4-dimethyl-$N_1$-ethoxycarbonyltrifluoromethanesulfonanilide, using steps (4) and (5).

5-Acetamido-2,4-dimethyltrifluoromethanesulfonanilide (7.75 g., 25 mmole) was added portionwise to a stirred suspension of sodium hydride oil dispersion (2.64 g., 55 mmole) in glyme under nitrogen atmosphere. This suspension was stirred for 2 hours at room temperature. Ethyl chloroformate (5.94 g., 55 mmoles) was slowly added. The reaction mixture was heated to its reflux temperature for four hours. The solvent was then removed under reduced pressure and the oily residue was recrystallized from hexane and benzene. The precipitate was collected by filtration, to give a solid, m.p. 73°–74° C.

| Elementary analysis: | | | |
|---|---|---|---|
| FOUND | | CALCULATED | |
| C | 45.2; | C | 44.9; |
| H | 4.7; | H | 4.6; |

| Elementary analysis: | | | |
|---|---|---|---|
| FOUND | | CALCULATED | |
| N | 6.1. | N | 6.2. |

The following additional compounds can be prepared utilizing step (5) but substituting the appropriate precursors.

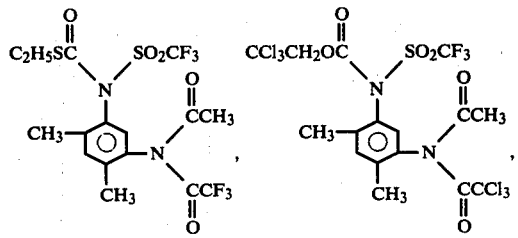

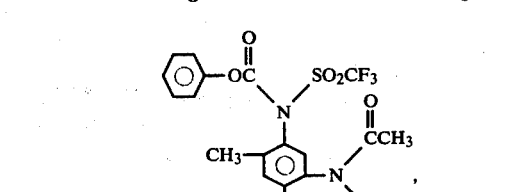

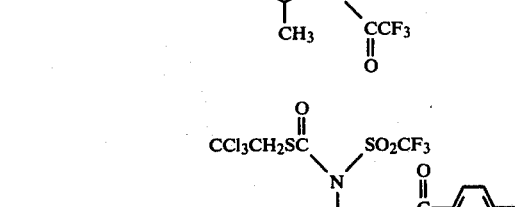

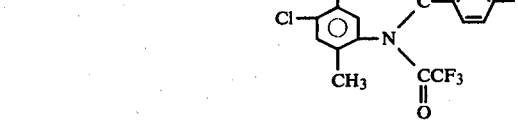

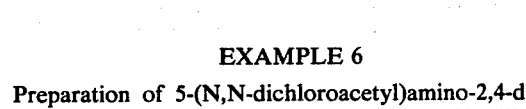

EXAMPLE 6

Preparation of 5-(N,N-dichloroacetyl)amino-2,4-dimethyltrifluoromethanesulfonanilide, steps (6), (7) and (8).

2,4-Dimethyl-5-nitroaniline was reduced in the presence of Raney nickel utilizing substantially the same conditions described in Example 2 to form 2,4-dimethyl-1,5-phenylenediamine and that compound was sulfonated under the conditions of Example 3. The resulting 5-amino-2,4-dimethyltrifluoromethanesulfonanilide (10.72 g., 40 mmole) was dissolved in 1,2-dichloroethane (60 ml.), and the solution was cooled to a temperature of 0° to 5° C. To this solution was slowly added chloroacetyl chloride (10.16 g., 90 mmole). The solution was then heated at its reflux temperature for 10 hours. Hexane (100 ml.) was added to the hot reaction mixture, the reaction mixture was then filtered while hot, and the solid product was collected upon crystallization, m.p. 170°–172° C.

| Elementary analysis: | | | |
|---|---|---|---|
| FOUND | | CALCULATED | |
| C | 37.0; | C | 37.0; |
| H | 3.1; | H | 3.1; |
| N | 6.6. | N | 6.6. |

The following compounds were also prepared utilizing steps (6), (7) and (8), but substituting the appropriate precursors:

5-(N,N-divaleryl)amino-2,4-dimethyltrifluoromethanesulfonanilide, m.p. 103°–105° C.;
5-(N,N-diacetyl)amino-2,4-dimethyltrifluoromethanesulfonanilide, m.p. 172°–173° C.;
5-(N,N-diacetyl)amino-2-chloro-4-methyltrifluoromethanesulfonanilide, m.p. 152°–154° C.; and
5-(N,N-dipropionyl)amino-2,4-dimethyltrifluoromethanesulfonanilide, m.p. 176°–178° C.

The following compounds can be prepared utilizing steps (6), (7), and (8), but substituting the appropriate precursor:

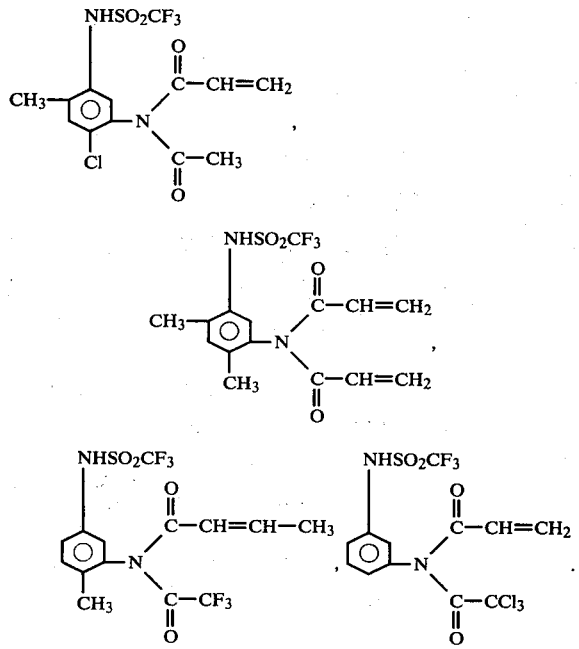

What is claimed is:
1. A compound of the formula:

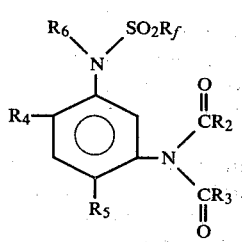

wherein
$R_f$ is lower perfluoroalkyl;
$R_2$ and $R_3$ each independently is
(1) a hydrocarbon group selected from alkyl; alkenyl; cycloalkyl; phenyl; and phenyl substituted by up to 3 groups selected from alkyl, alkoxy, alkylthio, mono- or dialkylamino, and halo wherein each alkyl moiety has 1 to 4 carbon atoms;
(2) haloalkyl;
(3) alkoxy; and
(4) a heterocyclic group which can contain only carbon, hydrogen, oxygen, nitrogen, and sulfur, but which must contain at least one ring atom selected from oxygen, nitrogen, and sulfur;
$R_4$ and $R_5$ each independently is hydrogen, alkyl, or halo; and
$R_6$ is hydrogen, alkoxycarbonyl, (alkylthio)carbonyl, (haloalkylthio)carbonyl, haloalkoxycarbonyl, or phenoxycarbonyl;
and agriculturally acceptable salts of the acid form compounds; provided that
$R_f$ contains not more than four carbon atoms,
$R_2$ and $R_3$ individually contain not more than nine carbon atoms,
$R_4$ and $R_5$ individually contain not more than four carbon atoms, and
$R_6$ contains not more than twelve carbon atoms.

2. The compound 5-(N,N-diacetyl)amino-2,4-dimethyltrifluoromethanesulfonanilide according to claim 1.

3. The compound 5-(N-acetyl-N-trifluoroacetyl)amino-2,4-dimethyltrifluoromethanesulfonanilide according to claim 1.

4. The compound 5-(N-acetyl-N-dichloroacetyl)amino-2,4-dimethyltrifluoromethanesulfonanilide according to claim 1.

5. The compound 5-(N-acetyl-N-chloroacetyl)amino-2,4-dimethyltrifluoromethanesulfonanilide according to claim 1.

6. The compound 5-(N-acetyl-N-valeryl)amino-2,4-dimethyltrifluoromethanesulfonanilide according to claim 1.

7. The compound 5-(N,N-diacetyl)amino-2-chloro-4-methyltrifluoromethanesulfonanilide according to claim 1.

8. The compound 5-(N-acetyl-N-cyclopropanecarbonyl)amino-2,4-dimethyltrifluoromethanesulfonanilide according to claim 1.

9. The compound 5-(N,N-dipropionyl)amino-2,4-dimethyltrifluoromethanesulfonanilide according to claim 1.

10. The compound 5-(N,N-divaleryl)amino-2,4-dimethyltrifluoromethanesulfonanilide according to claim 1.

11. The compound 5-(N-acetyl-N-ethoxycarbonyl)amino-2,4-dimethyl-$N_1$-ethoxycarbonyltrifluoromethanesulfonanilide according to claim 1.

12. A compound 5-(N-chloroacetyl-N-trifluoroacetyl)amino-2,4-dimethyltrifluoromethanesulfonanilide according to claim 1.

13. The compound 5-(N,N-dichloroacetyl)amino-2,4-dimethyltrifluoromethanesulfonanilide according to claim 1.

14. The compound 2,4-dimethyl-5-[N-(2'-furoyl)-N-acetyl]aminotrifuoromethanesulfonanilide according to claim 1.

15. The compound 2,4-dimethyl-5-[N-(4'-dimethylaminobenzoyl)-N-acetyl]aminotrifluoromethanesulfonanilide according to claim 1.

16. The compound 2-chloro-4-methyl-5-(N-benzoyl-N-trifluoroacetyl)aminotrifluoromethanesulfonanilide according to claim 1.

17. The compound 2-chloro-4-methyl-5-[N-(4'-methylthiobenzoyl)-N-trifluoroacetyl]aminotrifluoromethanesulfonanilide according to claim 1.

18. The compound 2-chloro-4-methyl-5-[N-(4'-methoxybenzoyl)-N-trifluoroacetyl)]aminotrifluoromethanesulfonanilide according to claim 1.

19. The compound 2-chloro-4-methyl-5-[N-(3'-nicotinyl)-N-acetyl]aminotrifluoromethanesulfonanilide according to claim 1.

20. The compound 2-chloro-4-methyl-5-[N-(2'-thienylcarbonyl)-N-trifluoroacetyl]aminotrifluoromethanesulfonanilide according to claim 1.

21. A method for terminating the life cycle of higher plants which comprises contacting said plants with an effective amount of a compound according to claim 1.

22. A herbicidal composition which comprises a compound according to claim 1 dispersed in an agriculturally acceptable extending medium.

23. A compound of the formula:

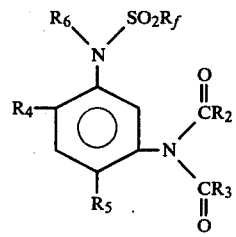

wherein
$R_f$ is trifluoromethyl;
$R_2$ and $R_3$ each independently is
(1) a hydrocarbon group selected from alkyl and cycloalkyl;
(2) haloalkyl; and
(3) alkoxy;
$R_4$ and $R_5$ each independently is hydrogen, alkyl, or halo; and
$R_6$ is hydrogen or alkoxycarbonyl; and agriculturally acceptable salts of the acid form compounds; provided that
$R_2$, $R_3$, $R_4$, $R_5$, and $R_6$ individually contain not more than four carbon atoms, for a sum total of not more then twelve carbon atoms.

* * * * *